(12) United States Patent
Ansmann et al.

(10) Patent No.: US 8,148,561 B2
(45) Date of Patent: Apr. 3, 2012

(54) COSMETIC OIL SUBSTANCES

(75) Inventors: Achim Ansmann, Erkrath (DE); Rolf Kawa, Monheim (DE); Lars Zander, Rommerskirchen (DE)

(73) Assignee: Cognis IP Management GmbH, Duesseldorf (DE)

( * ) Notice: Subject to any disclaimer, the term of this patent is extended or adjusted under 35 U.S.C. 154(b) by 1052 days.

(21) Appl. No.: 12/067,066

(22) PCT Filed: Sep. 6, 2006

(86) PCT No.: PCT/EP2006/008669
§ 371 (c)(1),
(2), (4) Date: Mar. 17, 2008

(87) PCT Pub. No.: WO2007/031220
PCT Pub. Date: Mar. 22, 2007

(65) Prior Publication Data
US 2008/0249172 A1 Oct. 9, 2008

(30) Foreign Application Priority Data

Sep. 15, 2005 (EP) .................................... 05020069
Nov. 2, 2005 (DE) ......................... 10 2005 052 173

(51) Int. Cl.
*C07C 57/00* (2006.01)
(52) U.S. Cl. ......................... 554/224; 554/223; 514/522
(58) Field of Classification Search .................. 514/522; 554/223, 224
See application file for complete search history.

(56) References Cited

FOREIGN PATENT DOCUMENTS
DE 4341794 C1 * 1/1995
* cited by examiner

*Primary Examiner* — Deborah D Carr
(74) *Attorney, Agent, or Firm* — Diehl Servilla LLC

(57) ABSTRACT

A storage-stable, smooth-feeling, non-comedogenic fatty acid ester mixture of 2-ethylhexanol and fatty acids comprising 2-ethylhexyl fatty acid esters, wherein the aggregate amount of $C_{12}$ and $C_{14}$ 2-ethylhexyl fatty acid esters is 85% or more of the mixture, based on the total weight of all fatty acid esters in the mixture, which mixtures are useful in or as an oil component of a cosmetic or pharmaceutical preparation.

22 Claims, No Drawings

US 8,148,561 B2

COSMETIC OIL SUBSTANCES

CROSS-REFERENCE TO RELATED APPLICATIONS

This application is filed under 35 U.S.C. §371, claiming priority from PCT/EP2006/008669 filed Sep. 6, 2006, which claims priority from EP 05020069 filed Sep. 15, 2005, and DE 102005052173.8 filed Nov. 2, 2005, the entire contents of these applications are incorporated herein by reference.

FIELD OF THE INVENTION

This invention relates to cosmetic ingredients and, more particularly, to fatty acid ester mixtures of 2-ethylhexanol and fatty acids, the aggregate amount of the $C_{12}$ and $C_{14}$ 2-ethylhexyl fatty acid esters being 85% or more in the mixture.

BACKGROUND AND RELATED ART

Consumers expect cosmetic skin- and hair-care emulsions to satisfy a range of requirements. Apart from the cleaning and skin-/hair-care effects, value is placed on such diverse parameters as very high dermatological compatibility, good lipid-layer-enhancing properties, elegant appearance, optimal sensory impression and stability in storage.

Besides a number of surfactants, preparations used to clean and care for the human skin and hair generally contain, above all, oil components and water. The oil components/emollients used include, for example, hydrocarbons, ester oils and vegetable and animal oils/fats/waxes. In order to meet stringent commercial requirements in regard to sensory properties and optimal dermatological compatibility, new oil components are continually being developed and tested.

Oils with good spreading properties are highly rated in the cosmetics industry because they are a key factor for sensorially-light preparations. Important representatives of this group are the isopropyl esters, such as isopropyl myristate (IPM) and isopropyl palmitate (IPP). Unfortunately, cosmetic chemists frequently criticize this group of products for their negative sensory impression, i.e., a distinctly audible grating sound when rubbed onto the skin and an associated unpleasant dry sensory impression. In addition, the isopropyl esters have the disadvantage of a comedogenic potential.

Other known oil components include fatty acid esters of 2-ethylhexanol, such as, for example, the esters of 2-ethylhexanol with stearic acid ($C_{18}$), which are commercially obtainable under the INCI name of ethylhexyl stearate (for example, Cetiol® 868 from Cognis; Crodamol® OS from Croda Inc. and Estol® 1514 from Uniquema).

Other known oil components include fatty acid esters of 2-ethylhexanol with lauric acid ($C_{12}$, dodecanoic acid) which are commercially obtainable under the INCI name of ethylhexyl laurate (for example, AEC ethylhexyl laurate from A. & E. Connock Ltd. and Estol® 3613 from Uniquema). Also known are fatty acid esters of 2-ethylhexanol with myristic acid ($C_{14}$, tetradecanoic acid), which are commercially obtainable under the INCI name of ethylhexyl myristate (for example, AEC ethylhexyl myristate from A. & E. Connock Ltd.). In addition, coconut oil fatty acid esters of 2-ethylhexanol are commercially obtainable under the INCI name of ethylhexyl cocoate (for example, Crodamol® OC from Croda Inc.). The product is a 2-ethylhexyl fatty acid ester with fatty acids of coconut oil. The fatty acid distribution of coconut oil has the following typical composition: $C_{12}$ (dodecanoic acid, lauric acid): 45-to-53%, by weight; $C_{14}$ (tetradecanoic acid, myristic acid): 15-to-21%, by weight; $C_{16}$ (palmitic acid): 74-to-11%, by weight; $C_{18:1}$ (oleic acid): 6-to-8%, by weight; $C_{18}$ (stearic acid): 2-to-4%, by weight; $C_{10}$ (decanoic acid): 5-to-10%, by weight; $C_8$ (octanoic acid): 5-to-10%, by weight, $C_6$ (hexanoic acid): under 1%, by weight (source: Ullmanns Encyclopedia of Industrial Chemistry, 2005, Wiley & Sons).

EP 0 732 912 B1 (WO 95/15743) describes mixtures of Guerbet alcohols with 2-ethylhexyl esters based on a fatty acid with the following C-chain distribution: >3%, by weight, $C_{14}$; 45-to-53%, by weight, $C_{16}$; 43-to-52%, by weight, $C_{18}$; and <2%, by weight, $C_{20}$.

The problem addressed by the present invention was to find a high-spreading oil which, as an oil component itself and in cosmetic and/or pharmaceutical preparations, leaves a smooth impression behind on the skin, imparts very little stickiness, rather high softness and no comedogenic potential. It has surprisingly been found that an ester mixture based on 2-ethylhexanol with fatty acids having a particular fatty acid distribution solves the problem addressed by the invention.

BRIEF SUMMARY OF THE INVENTION

The present invention is directed to fatty acid ester mixtures of 2-ethylhexanol and fatty acids, comprising 2-ethylhexyl fatty acid esters, wherein the aggregate amount of $C_{12}$ and $C_{14}$ 2-ethylhexyl fatty acid esters comprises 85% or more, preferably 90% or more, more preferably 95% or more, and preferably comprising 2-ethylhexyl fatty acid esters with a carbon chain length of 10 or less, in the aggregate, 3% or less, preferably 2% or less, more preferably 1.5% or less, and preferably comprising 2-ethylhexyl fatty acid esters with a carbon chain length of 16 or more, in the aggregate, 8% or less, preferably 4% or less, more preferably 3% or less, and most preferably 2% or less, all based on the total weight of all fatty acid esters in the mixture, as well as to the oil components of cosmetic and/or pharmaceutical preparations comprising such fatty acid mixtures.

DETAILED DESCRIPTION OF THE INVENTION

The present invention relates to fatty acid ester mixtures of 2-ethylhexanol and fatty acids, the aggregate amount of the $C_{12}$ and $C_{14}$ 2-ethylhexyl fatty acid esters being 85% or more, preferably 90% or more, and, more particularly, 95% or more, based on the total amount of all fatty acid esters in the mixture.

The remainder of the mixtures usually consists of fatty acid esters of 2-ethylhexanol with fatty acids having a carbon chain length of $C_4$ to $C_{22}$ and, more particularly, $C_6$ to $C_{20}$.

The present invention also relates to a fatty acid ester mixture of 2-ethylhexanol and fatty acids, the amount of the 2-ethylhexyl fatty acid esters with a C-chain length of 10 or less being 3% or less, preferably 2% or less, more preferably 1.5% or less, and most preferably 1% or less, based on the total weight of all fatty acid esters in the mixture.

The present invention also relates to a fatty acid ester mixture of 2-ethylhexanol and fatty acids, the amount of the 2-ethylhexyl fatty acid esters with a C-chain length of 16 or more being 8% or less, preferably 4% or less, more preferably 3% or less, and most preferably 2% or less, based on the total weight of all fatty acid esters in the mixture.

None of the known fatty acid ester mixtures has the 2-ethylhexyl fatty acid ester distribution according to the invention. It has surprisingly been found that not only are mixtures with the 2-ethylhexyl fatty acid ester distribution according to the invention high-spreading oil components, they also possess high softness, excellent personal (skin) care properties, dermatological compatibility and very little stickiness. In addition, these oil components have no comedogenic potential and can readily be incorporated in cosmetic formulations.

A preferred embodiment of the invention relates to fatty acid ester mixtures of 2-ethylhexanol and fatty acids, the aggregate amount of the $C_{12}$ and $C_{14}$ 2-ethylhexyl fatty acid esters being 85% or more, based on the total weight of all fatty acid esters in the mixture, and the amount of the 2-ethylhexyl fatty acid esters with a C-chain length of 10 or less being 3% or less, on the same basis.

Another preferred embodiment of the invention relates to fatty acid ester mixtures of 2-ethylhexanol and fatty acids, the aggregate amount of the $C_{12}$ and $C_{14}$ 2-ethylhexyl fatty acid esters being 85% or more, based on the total weight of all fatty acid esters in the mixture, and the amount of the 2-ethylhexyl fatty acid esters with a C-chain length of 16 or more being 8% or less, based on the total weight of all fatty acid esters in the mixture.

Still another preferred embodiment of the invention relates to fatty acid ester mixtures of 2-ethylhexanol and fatty acids, the aggregate amount of the $C_{12}$ and $C_{14}$ 2-ethylhexyl fatty acid esters being 85% or more, based on the total weight of all fatty acid esters in the mixture, and the amount of the 2-ethylhexyl fatty acid esters with a carbon chain length of 10 or less being 3% or less, and the amount of the 2-ethylhexyl fatty acid esters with a carbon chain length of 16 or more being 8% or less, based on the total weight of all fatty acid esters in the mixture.

In all these embodiments, the aggregate amount of the $C_{12}$ and $C_{14}$ 2-ethylhexyl fatty acid esters is preferably 90% or more, and, more particularly, 95% or more, based on the total weight of all fatty acid esters in the mixture.

In all these embodiments, the amount of the 2-ethylhexyl fatty acid esters with a carbon chain length of 10 or less is preferably 2% or less, more preferably 1.5% or less, and most preferably 1% or less, based on the total weight of all fatty acid esters in the mixture.

In all these embodiments, the sum of the 2-ethylhexyl fatty acid esters with a carbon chain length of 16 or more is preferably 4% or less, more preferably 3% or less, and most preferably 2% or less, based on the total weight of all fatty acid esters in the mixture.

The present invention also relates to fatty acid ester mixtures of 2-ethylhexanol and fatty acids, the 2-ethylhexyl fatty acid esters having the following C-chain distribution: (a) $C_{12}$: 60% or more, and (b) $C_{14}$: between 15% and 40%, based on the total weight of all fatty acid esters in the mixture.

In particularly preferred embodiments of the present invention, the amount of the $C_{12}$ fatty acid 2-ethylhexyl fatty acid esters is 65% or more, and, more particularly, 70% or more, based on the total weight of all fatty acid esters in the mixture.

Also in particularly preferred embodiments of the present invention, the amount of the $C_{14}$ fatty acid 2-ethylhexyl fatty acid esters is between 20% and 35%, and preferably between 25% and 30%, based on the total weight of all fatty acid esters in the mixture.

A preferred embodiment of the present invention relates to fatty acid ester mixtures of 2-ethylhexanol and fatty acids, the 2-ethylhexyl fatty acid esters having the following carbon chain distribution: (a) $C_{12}$: 60% or more, and (b) $C_{14}$: between 15 and 40%, and the amount of the 2-ethylhexyl fatty acid esters with a C-chain length of 10 or less being 3% or less, preferably 2% or less, and more preferably 1% or less, based on the total weight of all fatty acid esters in the mixture.

Another preferred embodiment of the present invention relates to fatty acid ester mixtures of 2-ethylhexanol and fatty acids, the 2-ethylhexyl fatty acid esters having the following carbon chain distribution: (a) $C_{12}$: 60% or more, and (b) $C_{14}$: between 15 and 40%, and the amount of the 2-ethylhexyl fatty acid esters with a carbon chain length of 16 or less being 8% or less, preferably 4% or less, more preferably 3% or less, still more preferably 2% or less, and most preferably 1% or less, based on the total weight of all fatty acid esters in the mixture.

A particularly preferred embodiment of the present invention relates to fatty acid ester mixtures of 2-ethylhexanol and fatty acids, the 2-ethylhexyl fatty acid esters having the following carbon chain distribution: (a) $C_{12}$: 60% or more, and (b) $C_{14}$: between 15 and 40%, and the amount of the 2-ethylhexyl fatty acid esters with a carbon chain length of 16 or less being 3% or less, particularly 2% or less, and preferably 1% or less, based on the total weight of all fatty acid esters in the mixture, and the amount of the 2-ethylhexyl fatty acid esters with a carbon chain length of 16 or more being 8% or less, particularly 4% or less, preferably 3% or less, more preferably 2% or less and most preferably 1% or less, based on the total weight of all fatty acid esters in the mixture.

Production

The fatty acid ester mixtures according to the invention are produced by processes known to the practitioner. The fatty acid ester mixtures may be produced, for example, by esterification of 2-ethylhexanol with fatty acid mixtures, the fatty acid mixtures having the fatty acid distribution according to the invention, which then reappears in the fatty acid-2-ethylhexyl ester mixture. They may also be produced by transesterification of 2-ethylhexanol with a fatty acid methyl ester mixture, the fatty acid methyl ester mixture used for production having the fatty acid distribution according to the invention. In addition, the fatty acid ester mixtures according to the invention may be obtained by mixing the corresponding individual fatty acid-2-ethylhexyl esters.

The odor of the products obtained by esterification or transesterification may be improved as required by deodorization. Similarly, the color of the products may be improved, as necessary, by treatment with methods also known to the practitioner.

Typical fatty acid mixtures or fatty acid methyl ester mixtures suitable for the production of the fatty acid-2-ethylhexyl ester mixtures according to the invention have the following carbon chain distribution, by weight, for example: $C_6$-to-$C_{10}$ fatty acids: less than 3%, $C_{12}$ fatty acids: 60-to-80%, $C_{14}$ fatty acids: 15-to-40%, $C_{16}$ fatty acids: 4% or less, and fatty acids with a C-chain lengths >16: 0.5% or less.

Fatty acid mixtures suitable for the production of the ester mixtures according to the invention are commercially obtainable under the name of Edenor® C12 70 (from Cognis), and have the following fatty acid distribution, by weight, based on the total weight of the fatty acids in the product: fatty acids with a C-chain length of $\leq 10$ is 2%, preferably $\leq 1\%$; $C_{12}$ fatty acids: between 65 and 77%, preferably 68%; $C_{14}$ fatty acids: between 19 and 34%, preferably 28%; $C_{16}$ fatty acids $\leq 4\%$, more particularly $\leq 3\%$.

In the context of the present specification, the expression "$C_X$ fatty acids" encompasses all carboxylic acids which have a carbon chain length of "X". For example, the expression "$C_{12}$ fatty acids" encompasses all carboxylic acids with a C-chain length of 12. The same interpretation applies to the expression "C-$_Y$ fatty acid-2-ethylhexyl ester".

Aliphatic, aromatic, saturated, mono- and polyunsaturated, linear and branched fatty acids are all included. A preferred embodiment of the invention is characterized by the use of mainly (i.e., generally >90% of the particular fatty acid) aliphatic, linear carboxylic acids with the carbon chain length mentioned, such as, for example, lauric acid as a $C_{12}$ fatty acid and myristic acid as a $C_{14}$ fatty acid.

Cosmetic and/or Pharmaceutical Preparations

Stable cosmetic and pharmaceutical emulsions may be produced using the fatty acid-2-ethylhexyl ester mixtures according to the invention.

Accordingly, the present invention also relates to the use of the fatty acid-2-ethylhexyl ester mixtures according to the invention in cosmetic and/or pharmaceutical preparations, more particularly as the oil component of such preparations. The fatty acid-2-ethylhexyl ester mixtures according to the invention may be used either as the sole oil component or in combination with other oil components, depending on the preparation.

The fatty acid-2-ethylhexyl ester mixtures according to the invention may be used in cosmetic and/or pharmaceutical preparations in concentrations of 1-to-90%, preferably in concentrations of 1-to-50%, and more particularly in concentrations of 2-to-20%, based on the total weight of the cosmetic and/or pharmaceutical preparation. Applications include, for example, cosmetic and/or pharmaceutical oil-in-water or water-in-oil emulsions for personal, particularly skin, care, sun protection formulations, antiperspirant/deodorant compositions, formulations for makeup, oily preparations for personal (skin) care, impregnating liquids for such substrates as, for example, paper and nonwoven products, such as wet wipes, handkerchiefs, diapers or hygiene products.

The fatty acid-2-ethylhexyl ester mixtures according to the invention are suitable, in particular, for a sprayable application and/or as a personal care emulsion for tissues, papers, wipes, sponges (for example, polyurethane sponges), plasters for use in baby hygiene or baby care, skin care, sun protection, after-sun treatment, insect repellents, facial or body cleansing and antiperspirant/deodorant applications. The use of the fatty acid-2-ethylhexyl ester mixtures according to the invention has a positive effect on sensory behavior on application.

The cosmetic and/or pharmaceutical preparations may be body care formulations, for example, in the form of a body milk, creams, lotions, sprayable emulsions, products for eliminating body odor, etc. The fatty acid-2-ethylhexyl ester mixtures may also be used in surfactant-containing formulations, such as, for example, foam and shower baths, hair shampoos and rinses for skin care. Depending on the particular application envisaged, the cosmetic formulations may contain a number of other auxiliaries and additives, such as, for example, surfactants, other oil components, emulsifiers, pearlizing waxes, consistency factors, thickeners, superfatting agents, stabilizers, polymers, fats, waxes, lecithins, phospholipids, biogenic agents, UV protection factors, antioxidants, deodorants, antiperspirants, antidandruff agents, film formers, swelling agents, insect repellents, self-tanning agents, tyrosinase inhibitors (depigmenting agents), hydrotropes, solubilizers, preservatives, perfume oils, dyes, etc.

The surface-active substances present may be anionic, nonionic, cationic and/or amphoteric or zwitterionic surfactants. In surfactant-containing cosmetic preparations such as, for example, shower gels, foam baths, shampoos, etc., at least one anionic surfactant is preferably present. In this case, the percentage content of surfactants is normally about 1-to-30%, preferably 5-to-25%, and more preferably 10-to-20%, by weight.

Typical examples of anionic surfactants include soaps, alkyl benzene sulfonates, alkanesulfonates, olefin sulfonates, alkylether sulfonates, glycerol ether sulfonates, α-methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution.

Typical examples of nonionic surfactants include fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partly-oxidized alk(en)yl oligoglycosides or glucuronic acid derivatives, fatty acid-N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution.

Typical examples of cationic surfactants include quaternary ammonium compounds, for example, dimethyl distearyl ammonium chloride, and esterquats, more particularly quaternized fatty acid trialkanolamine ester salts.

Typical examples of amphoteric or zwitterionic surfactants include alkylbetaines, alkylamidobetaines, aminopropionates, aminoglycinates, imidazolinium betaines and sulfobetaines. The surfactants mentioned are all known compounds. Information on their structure and production may be found in relevant synoptic works in this field. Typical examples of particularly suitable mild, i.e., particularly dermatologically compatible, surfactants include fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefin sulfonates, ether carboxylic acids, alkyl oligoglucosides, fatty acid glucamides, alkylamidobetaines, amphoacetals and/or protein fatty acid condensates, preferably based on wheat proteins.

Body care preparations, such as creams, lotions and milks, normally contain a number of other oil components and emollients which contribute towards further optimizing their sensory properties. The oil components are normally present in a total quantity of 0.1-to-90%, preferably 1-to-50%, more preferably 5-to-25%, and most preferably 5-to-15%, by weight. Suitable other oil components include, for example, Guerbet alcohols based on fatty alcohols containing 6-to-18, and preferably 8-to-10 carbon atoms, esters of linear $C_{6-22}$ fatty acids with linear or branched $C_{6-22}$ fatty alcohols or esters of branched $C_{6-13}$ carboxylic acids with linear or branched $C_{6-22}$ fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of $C_{18-38}$ alkylhydroxycarboxylic acids with linear or branched $C_{6-22}$ fatty alcohols, more especially dioctyl malate, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-, di- and triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1-to-22 carbon atoms or polyols containing 2-to-10 carbon atoms and 2-to-6 hydroxyl groups, vegetable oils, branched primary alcohols, substituted cyclohexanes, linear and branched $C_{6-22}$ fatty alcohol carbonates, such as dicaprylyl carbonate (Cetiol® CC), for example, Guerbet carbonates based on $C_{6-18}$ and preferably $C_{8-10}$ fatty alcohols, esters of benzoic acid with linear and/or branched C-22 alcohols (for example, Finsolv® TN), linear or branched, symmetrical or nonsymmetrical dialkyl ethers containing 6-to-22 carbon atoms per alkyl group, such as dicaprylyl carbonate (Cetiol® OE), for example, ring-opening products of epoxidized fatty acid esters with polyols.

Fats and waxes are added to the body care products both as care components and to increase the consistency of the cosmetic preparations. Typical examples of fats include glycerides, i.e., solid, vegetable or animal products which consist essentially of mixed glycerol esters of higher fatty acids. Fatty acid partial glycerides, i.e., technical mono- and/or diesters of glycerol with $C_{12-18}$ fatty acids, such as, for example, glycerol mono/dilaurate, palmitate or stearate, may also be used for this purpose. Suitable waxes include, inter alia, natural waxes, such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically-modified waxes (hard waxes), such as, for example, montan ester waxes, sasol waxes, hydrogenated jojoba waxes and synthetic waxes, such as, for example, polyalkylene waxes and polyethylene glycol waxes.

Besides the fats, other suitable additives include fat-like substances, such as lecithins and phospholipids. Examples of natural lecithins include the kephalins, which are also known as phosphatidic acids and which are derivatives of 1,2-diacyl-sn-glycerol-3-phosphoric acids. By contrast, phospholipids are generally understood to be mono- and preferably diesters of phosphoric acid with glycerol (glycerophosphates), which are normally classed as fats. Sphingosines and sphingolipids are also suitable.

Suitable thickeners include, for example, Aerosil® hydrophilic silicas, polysaccharides, more especially xanthan gum, guar-guar, agar-agar, alginates and tyloses, carboxymethyl cellulose and hydroxyethyl and hydroxypropyl cellulose, polyvinyl alcohol, polyvinyl pyrrolidone and bentonites, such as, for example, Bentone® Gel VS-5PC (Rheox).

UV protection factors in the context of the invention include, for example, organic substances (light filters), which are liquid or crystalline at room temperature and which are capable of absorbing ultraviolet radiation and of releasing the energy absorbed in the form of longer-wave radiation, for example, heat. UV-B filters may be oil-soluble or water-soluble. The following are examples of oil-soluble UV-B filters:

3-benzylidene camphor or 3-benzylidene norcamphor and derivatives thereof, for example, 3-(4-methylbenzylidene)-camphor, as described in EP 0693471 B1;

4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester;

esters of cinnamic acid, preferably 4-methoxycinnamic acid-2-ethylhexyl ester, 4-methoxycinnamic acid propyl ester, 4-methoxycinnamic acid isoamyl ester, and 2-cyano-3,3-phenylcinnamic acid-2-ethylhexyl ester (octocrylene);

esters of salicylic acid, preferably salicylic acid-2-ethylhexyl ester, salicylic acid-4-isopropylbenzyl ester, and salicylic acid homomethyl ester;

derivatives of benzophenone, preferably 2-hydroxy-4-methoxybenzophenone, 2-hydroxy-4-methoxy'-methylbenzophenone, and 2,2'-dihydroxy-4-methoxybenzophenone;

esters of benzalmalonic acid, preferably 4-methoxybenzalmalonic acid di-2-ethylhexyl ester;

triazine derivatives, such as, for example, 2,4,6-trianilino-(p-carbo-2'-ethyl-1'-hexyloxy)-1,3,5-triazine and octyl triazone, as described in EP 0818450 A1, or dioctyl butamido triazone (Uvasorb® HEB);

propane-1,3-diones, such as, for example, 1-(4-tert.butylphenyl)-3-(4'-methoxyphenyl)-propane-1,3-dione; and ketotricyclo(5.2.1.0)decane derivatives, as described in EP 0694521 B1.

Suitable water-soluble UV-B filters include:

2-phenylbenzimidazole-5-sulfonic acid and alkali metal, alkaline earth metal, ammonium, alkylammonium, alkanolammonium and glucammonium salts thereof;

sulfonic acid derivatives of benzophenones, preferably 2-hydroxy-4-methoxybenzophenone-5-sulfonic acid and salts thereof; and sulfonic acid derivatives of 3-benzylidene camphor, such as, for example, 4-(2-oxo-3-bornylidenemethyl)-benzene sulfonic acid and 2-methyl-5-(2-oxo-3-bornylidene)-sulfonic acid, and salts thereof.

Typical UV-A filters include, in particular, derivatives of benzoyl methane such as, for example, 1-(4'-tert.butylphenyl)-3-(4'-methoxyphenyl)-propane-1,3-dione, 4-tert.butyl-4'-methoxydibenzoyl methane (Parsol® 1789) or 1-phenyl-3-(4'-isopropylphenyl)-propane-1,3-dione and the enamine compounds described in DE 19712033 A1 (BASF).

The UV-A and UV-B filters may, of course, also be used in the form of mixtures. Particularly favourable combinations consist of the derivatives of benzoyl methane, for example, 4-tert.butyl-4'-methoxydibenzoylmethane (Parsol® 1789) and 2-cyano-3,3-phenylcinnamic acid-2-ethyl hexyl ester (octocrylene) in combination with esters of cinnamic acid, preferably 4-methoxycinnamic acid-2-ethyl hexyl ester and/or 4-methoxycinnamic acid propyl ester and/or 4-methoxycinnamic acid isoamyl ester. Combinations, such as these, are advantageously combined with water-soluble filters, such as, for example, 2-phenylbenzimidazole-5-sulfonic acid and alkali metal, alkaline earth metal, ammonium, alkylammonium, alkanolammonium and glucammonium salts thereof.

Particularly suitable broad-spectrum sun filters include 2,2'-methylene-bis-[4-(1,1,3,3-tetramethylbutyl)-6-(2H-benzotriazol-2-yl)-phenol] (Tinosorb® M) and 2,2'-[6-(4-methoxyphenyl)-1,3,5-triazine-2,4-diyl]-bis-[5-[(2-ethylhexyl)-oxy]-phenol (Tinosorb® S).

Besides the soluble substances mentioned, insoluble light-blocking pigments, i.e., finely-dispersed metal oxides or salts, may also be used for this purpose. Examples of suitable metal oxides include, in particular, zinc oxide and titanium dioxide, and also oxides of iron, zirconium, silicon, manganese, aluminium and cerium and mixtures thereof. Silicates (talcum), barium sulfate and zinc stearate may be used as salts. The oxides and salts are used in the form of the pigments for skin-care and skin-protecting emulsions and decorative cosmetics. The particles should have a mean diameter of less than 100 nm, preferably between 5 and 50 nm, and more preferably between 15 and 30 nm. They may be spherical in shape, although ellipsoidal particles or other non-spherical particles may also be used. The pigments may also be surface-treated, i.e., hydrophilicized or hydrophobicized. Typical examples include coated titanium dioxides, for example, Titandioxid T 805 (Degussa) and Eusolex® T2000 (Merck). Suitable hydrophobic coating materials include, above all, silicones and, among these, especially trialkoxyoctylsilanes or simethicones. So-called micro- or nanopigments are preferably used in sun protection products. Micronized zinc oxide is preferably used. Other suitable UV protection factors are mentioned in P. Finkel's overview in SÖFW-Journal 122, 543 (1996) and in Parf. Kosm. 3, 11 (1999).

Besides the two groups of primary sun protection factors mentioned above, secondary sun protection factors of the antioxidant type, which interrupt the photochemical reaction chain that is initiated when UV rays penetrate into the skin, may also be used. Typical examples include amino acids (for example, glycine, histidine, tyrosine, and tryptophane) and derivatives thereof, imidazoles (for example, urocanic acid) and derivatives thereof, peptides, such as D,L-carnosine, D-carnosine, L-carnosine and derivatives thereof (for example, anserine), carotinoids, carotenes (for example, α-carotene, β-carotene, and lycopene) and derivatives thereof, chlorogenic acid and derivatives thereof liponic acid and derivatives thereof (for example, dihydroliponic acid), aurothioglucose, propylthiouracil and other thiols (for example, thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example, butionine sulfoximines, homocysteine sulfoximine, butionine sulfones, penta-, hexa- and hepta-thionine sulfoximine) in very small compatible dosages (for example, pmol to μmol/kg).

Other examples include (metal) chelators (for example, α-hydroxyfatty acids, palmitic acid, phytic acid, and lactoferrine), α-hydroxy acids (for example, citric acid, lactic acid, and malic acid), humic acid, bile acid, bile extracts, bilirubin, biliverdin, EDTA, EGTA and derivatives thereof, unsaturated fatty acids and derivatives thereof (for example, γ-linolenic acid, linoleic acid, and oleic acid), folic acid and derivatives thereof, ubiquinone and ubiquinol and derivatives thereof vitamin C and derivatives thereof (for example, ascorbyl palmitate, Mg ascorbyl phosphate, ascorbyl acetate), tocopherols and derivatives (for example, vitamin E acetate), vitamin A and derivatives (vitamin A palmitate) and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof superoxide dismutase, zinc and derivatives thereof (for example, ZnO, $ZnSO_4$), selenium and derivatives thereof (for example, selenium methionine), stilbenes and derivatives thereof (for example, stilbene oxide, and trans-stilbene oxide) and derivatives of these active substances suitable for the purposes of the invention (salts, esters, ethers, sugars, nucleotides, nucleosides, peptides and lipids).

In the context of the invention, biogenic agents include, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, for example, prunus extract, bambara nut extract, and vitamin complexes.

Deodorizing agents counteract, mask or eliminate body odors that are formed through the action of skin bacteria on apocrine perspiration which results in the formation of unpleasant-smelling degradation products. Accordingly, suitable deodorizing agents include, inter alia, germ inhibitors, enzyme inhibitors, odor absorbers and odor maskers.

Suitable insect repellents include, for example, N,N-diethyl-m-toluamide, pentane-1,2-diol or 3-(N-n-butyl-N-acetylamino)-propionic acid ethyl ester), which is marketed as Insect Repellent® 3535 by Merck KGaA, and butylacetylaminopropionate.

A suitable self-tanning agent is dihydroxyacetone. Suitable tyrosine inhibitors which prevent the formation of melanin and are used in depigmenting agents include, for example, arbutin, ferulic acid, koji acid, coumaric acid and ascorbic acid (vitamin C).

Suitable preservatives include, for example, phenoxyethanol, formal-dehyde solution, parabens, pentanediol or sorbic acid and the silver complexes known under the name of Surfacine® and the other classes of compounds listed in Appendix 6, Parts A and B of the Kosmetikverordnung ("Cosmetics Directive").

Suitable perfume oils include mixtures of natural and synthetic perfumes. Natural perfumes include the extracts of blossoms, stems and leaves, fruits, fruit peels, roots, woods, herbs and grasses, needles and branches, resins and balsams. Animal raw materials, for example, civet and beaver, and synthetic perfume compounds of the ester, ether, aldehyde, ketone, alcohol and hydrocarbon type, are also suitable.

Suitable pearlizing waxes, particularly for use in surfactant-containing formulations include, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6-to-22 carbon atoms, especially long-chain esters of tartaric acid; fatty compounds, such as, for example, fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring-opening products of olefin epoxides containing 12-to-22 carbon atoms with fatty alcohols containing 12-to-22 carbon atoms and/or polyols containing 2-to-15 carbon atoms and 2-to-10 hydroxyl groups, and mixtures thereof.

Superfatting agents may be selected from such substances as, for example, lanolin and lecithin and also polyethoxylated or acylated lanolin and—lecithin derivatives, polyol fatty acid esters, monoglycerides and fatty acid alkanolamides, the fatty acid alkanolamides also serving as foam stabilizers.

Metal salts of fatty acids, such as, for example, magnesium, aluminium and/or zinc stearate or ricinoleate may be used as stabilizers.

In addition, hydrotropes, for example, ethanol, isopropyl alcohol or polyols, may be used to improve flow behavior. Suitable polyols preferably contain 2-to-15 carbon atoms and at least two hydroxyl groups. The polyols may contain other functional groups, more especially amino groups, or may be modified with nitrogen.

The following are intended to exemplify the invention, without, in any way, limiting it.

EXAMPLES

Example A According to the Invention

Production 1300 g 2-ethylhexanol and 1750 g of a fatty acid mixture (Edenor® C12 70%, from Cognis), with the following fatty acid distribution: $C_{10}$: $\le$2%, $C_{12}$: 65-77%, $C_{14}$: 19-34%, $C_{16}$: $\le$4%, were introduced into a reaction vessel under normal pressure in the presence of a color inhibitor (0.41 g hypophosphorous acid) and a catalyst (0.25 g tin(II) oxide). The mixture was heated under nitrogen to 245° C. When the acid number had fallen below 10, a vacuum of 300 mbar was applied; when the acid number had fallen below 1.5, the phase separator was by-passed; and when the acid number had fallen below 1, the excess 2-ethylhexanol was distilled off (at ca. 5 mbar).

In the refining vessel, the catalyst was precipitated with phosphoric acid (75% of the quantity of tin(II) oxide) and 200 l water. Dying was carried out at 85° C./ca. 5-to-50 mbar.

Comparison Example B

The commercially-available product Crodamol® OC (from Croda) was used for comparison. The following Table shows the carbon chain distribution of Examples A and C according to the invention and the Comparison Example B (ethyhexyl fatty acid ester, INCI: Ethylhexyl Cocoate, from Croda).

|  | Example A according to the invention | Example C according to the invention | Comparison Example B Crodamol ® OC. (Croda) |
|---|---|---|---|
| C6 [%] | Sum of the fatty acids with $C \le C8 < 0.5\%$ | 0 | 0.1 |
| C8 [%] |  | 0 | 4.2 |
| C10 [%] | <1% | 0.1 | 6.9 |
| C12 [%] | 68 | 73.4 | 47.6 |
| C14 [%] | 28 | 25.3 | 20.5 |
| C16 [%] | 2 | Amount of the fatty acids with | 12.6 |
| C18 [%] | Amount of the fatty acids | | 1.4 |
| C18:1 [%] | with $C > C_{18}$ is <0.5% | $C \ge C_{16} = 1.2$ | 6.3 |
| C18:2 [%] |  |  | 0.5 |

Example 1

Sensory Evaluation

The sensory evaluation of the product from Example A according to the invention was carried out against the product from Comparison Example B and isopropyl myristate, a typical cosmetic oil component.

A panel of 12 experts carried out the sensory evaluation. They examined the following five criteria, based on the final feeling on the skin:
1—spreading, 2—negative sensory impression, 3—stickiness, 4—softness, 5—positive sensory feeling. These criteria were evaluated with scores of 1 (poor) to 7 (good).

| Criterion | Isopropyl palmitate | Example A according to the invention | Comparison Example B Crodamol ® OC (Croda) |
|---|---|---|---|
| Spreading | 7 | 7 | 3 |
| Negative sensory impression | 7 | 1 | 1 |
| Stickiness | 3 | 1 | 3 |
| Softness | 2 | 7 | 3 |
| Care feeling | 2 | 7 | 3 |

The product from Example A according to the invention shows good softness and a good sensory feel compared with the prior art product, coupled with very good spreading properties and favorable sensory properties (inter alia, minimal stickiness).

Example 2

Sensory Evaluation in Cosmetic Formulations

The following cosmetic emulsions were prepared for evaluation of the sensory parameters.

|  | INCI | Formulation 1 (invention) | Formulation 2 | Formulation 3 |
|---|---|---|---|---|
| Emulgade ® SE-PF (Cognis) | Glyceryl Stearate (and) Ceteareth-20 (and) Ceteareth-12 (and) Cetearyl Alcohol (and) Cetyl Palmitate | 6.0 | 6.0 | 6.0 |
| Ethylhexyl ester from Production Example A |  | 16.0 | — | — |
| Comparison Example B Crodamol ® OC (Croda) | Ethylhexylcocoate | — | 16.0 | — |
| Isopropylpalmitate |  | — | — | 16.0 |
| Cosmedia ® SP (Cognis) | Sodium polyacrylate | 0.2 | 0.2 | 0.2 |
| Glycerin |  | 3.0 | 3.0 | 3.0 |
| Water, preservative |  | 74.8 | 74.8 | 74.8 |

All quantities are in % by weight. Emulgade® SE-PF and the particular oil component were melted at 75° C. Cosmedia® SP was uniformly stirred in. Water and glycerin, also at 75° C., were added to the oil phase and homogeneously stirred, followed by cooling. A homogenizing step was carried out at ca. 55° C. using a suitable rotor/stator system. The preservative was added either at 75° C. or at 40° C., depending on the sensitivity to temperature of the components in the particular formulation.

The sensory evaluation was carried out as described above.

| Criteria | Formulation 1 (according to the invention) | Formulation 2 (Ethylhexyl Cocoate, Crodamol ® OC) | Formulation 3 (Isopropylpalmitate) |
|---|---|---|---|
| Spreading | 6 | 3 | 5 |
| Negative sensory impression | 1 | 1 | 3 |
| Stickiness | 1 | 3 | 1 |
| Softness | 7 | 3 | 3 |

Cosmetic Preparations: Formulations for Spray and Wipe Applications and for Antiperspirant/Deodorant Compositions Formulations 1 to 26 represent stable formulations based on the oil component according to the invention, more particularly as produced in Example A, which are particularly suitable for a sprayable application and/or as an emulsion for personal (skin) care in tissues, papers, wipes, sponges (for example, polyurethane sponges), plasters for use in baby hygiene and baby care, skin care, sun protection, after-sun treatment, insect repellents, body and facial cleansing and antiperspirant/deodorant applications. Through the use of the oil component according to the invention, sensory behavior on application is positively influenced. The quantities shown are based on %, by weight, of the commercially-available substances in the composition as a whole.

TABLE 1

Formulations 1 to 13

| Component INCI (trade name) | 1 | 2 | 3 | 4 | 5 | 6 | 7 | 8 | 9 | 10 | 11 | 12 | 13 |
|---|---|---|---|---|---|---|---|---|---|---|---|---|---|
| Emulgade ® SE | | | | | | | | | | | | 10.7 | 5.1 |
| Eumulgin ® B2 | | | | | | | | | | | | 5.8 | 3.4 |
| Emulgade ® PL 68/50 | 1 | | 1 | 1 | | 2 | 2 | | 2 | | 2 | | |
| Eumulgin ® VL 75 | | 1 | | | 1 | | | 3 | | 2.5 | | | |
| Lanette ® E | 1 | 1 | 1 | | 1 | | | | | 1 | 1 | | |
| Oil component from Example A | 5 | 4 | 8 | 3 | 5 | 8 | 4 | 2 | 4 | 3 | 5 | 10 | 2 |
| Cetiol ® CC | 5 | 5 | 5 | | | | | 4 | | 5 | 3 | 4 | |
| Myritol ® 331 | 3 | 4 | | 4 | 4 | | | | 5 | | | 3 | 3 |
| Cetiol ® OE | | | | | 5 | | 3 | | 2 | | | | |
| Cetiol ® B | | | | 4 | | | | 4 | | 4 | | | |
| Cosmedia ® DC | 1 | 1 | 1 | 1 | 1 | 1.5 | 1.5 | 2 | 3 | 2 | 1.5 | 2 | 2 |
| Insect Repellent ® 3535 | | | | | | | | | | | 5 | 5 | |
| Copherol ® F1300 C | 1 | 1 | 1 | 1 | 1 | 1 | 1 | 1 | 1 | 1 | 1 | 1 | 1 |
| Zink oxide NDM | 5 | 5 | 5 | 5 | 5 | | 2 | | 5 | 3 | | | |
| Eusolex ® T 2000 | | | | 5 | 5 | | 2 | 3 | 5 | 2 | | | |
| Neo Heliopan ® AV | 7.5 | 7.5 | 7.5 | | | 3 | 1 | 3 | 5 | | | 5 | 5 |
| Neo Heliopan ® AV | 9 | 9 | 9 | | 2 | 1 | | | | | 2 | | 1.5 |
| Parsol ® 1789 | | | | | 2 | 2 | | | | 1 | 2 | 2 | |
| Neo Heliopan ® MBC | | | | | | 2 | | | | | | | 2 |
| Uvinul ® T 150 | | | | | 1 | 1 | 2 | | | | 1 | | |
| Uvasorb ® HEB | | | | | 1 | 1 | 2 | | | | 1 | 2 | |
| Neo Heliopan ® Hydro - Na-Salz, 15% aqueous solution | | | | | | | | | | | | | 13.3 |
| Glycerin | 3 | 3 | 3 | 3 | 3 | 3 | 3 | 3 | 3 | 3 | 3 | 5 | 5 |
| Veegum ® plus | 0.75 | 0.75 | | 0.5 | 0.5 | | 0.5 | | | 0.35 | | | |
| Keltrol T | 0.25 | 0.25 | | 0.5 | 0.5 | | 0.5 | | | 0.35 | | | |
| Cosmedia ® SP | | | 0.1 | | | 0.1 | 0.2 | | | | 0.1 | | |
| Pemulen ® TR-2 Polymer | | | | | | | | 0.2 | 0.1 | | | | |
| Water, perfume, preservative | q.s. | q.s. | q.s. | q.s. | q.s. | q.s. | q.s. | q.s. | q.s. | q.s. | q.s. | q.s. | q.s. |

TABLE 2

Formulations 14 to 26

| Component INCI (trade name) | 14 | 15 | 16 | 17 | 18 | 19 | 20 | 21 | 22 | 23 | 24 | 25 | 26 |
|---|---|---|---|---|---|---|---|---|---|---|---|---|---|
| Emulgade ® SE | 3.7 | 3.7 | | | | | | | | | | 4.9 | 4.1 |
| Eumulgin ® B1 | 1.3 | 1.3 | | | | | | | | | | | |
| Eumulgin ® B2 | | | | | | | | | | | | 1.1 | 0.9 |
| Emulgade ® PL 68/50 | | | 5 | 1 | 1 | 1 | 1 | 3 | | | | | |
| Eumulgin ® VL 75 | | | | | | | | | 3 | 5 | 5 | | |
| Lanette ® E | | | | 0.25 | 0.25 | 0.25 | 0.25 | .25 | | | | | |
| Amphisol K | | | 0.5 | | | | | | | | | | |

TABLE 2-continued

Formulations 14 to 26

| Component INCI (trade name) | 14 | 15 | 16 | 17 | 18 | 19 | 20 | 21 | 22 | 23 | 24 | 25 | 26 |
|---|---|---|---|---|---|---|---|---|---|---|---|---|---|
| Oil component from Example A | 4 | 5 | 6 | 8 | 5 | 8 | 8 | 10 | 7 | 4 | 10 | 5 | 5 |
| Cetiol ® CC | 5 |  | 5 |  |  |  |  |  | 2.5 | 4 | 4 | 5 | 5 |
| Cetiol ® LC |  |  |  | 1 | 1 | 1 | 1 | 1 |  |  |  |  |  |
| Myritol ® 312 |  |  |  | 1 | 1 | 1 | 1 | 1 |  |  |  |  |  |
| Myritol ® 331 |  |  |  |  |  |  |  |  |  | 4 | 4 |  |  |
| Cetiol ® SN | 3 | 3 | 3.5 |  |  |  |  |  |  |  |  |  |  |
| Eutanol ® G |  |  |  |  |  |  |  |  | 3.5 | 2 | 2 |  |  |
| Eutanol ® G16 |  |  |  | 1 | 1 | 1 | 1 | 1 |  |  |  |  |  |
| Cegesoft ® PS6 |  | 1.5 | 1.5 |  |  |  |  |  |  |  |  |  |  |
| Cegesoft ® PFO | 1.5 |  |  |  |  |  |  |  |  |  |  |  |  |
| Silikonöl Wacker AK ® 350 |  |  |  | 0.5 | 0.5 | 0.5 | 0.5 | 0.5 |  |  |  |  |  |
| Cosmedia ® DC | 1 |  | 1.5 |  |  |  |  | 1.5 |  | 2.5 | 2.5 |  | 0.5 |
| Hydagen ® C.A.T |  |  |  |  |  |  |  |  |  |  |  | 1.5 |  |
| Copherol ® F 1300 C |  |  |  |  |  |  |  |  | 0.5 | 0.5 | 0.5 |  |  |
| Copherol ® 1250 C | 0.5 | 0.5 |  |  |  |  |  |  |  |  |  |  |  |
| Ethanol |  |  |  |  |  |  |  |  |  |  |  | 5 |  |
| Locron ® L |  |  |  |  |  |  |  |  |  |  |  |  | 40 |
| Hydagen ® DCMF |  |  |  |  |  |  |  |  |  |  |  | 0.1 |  |
| Glycolic Acid |  |  |  |  |  |  |  |  |  |  |  | 0.04 |  |
| Glycerin | 2 | 2 | 2 | 3 | 3 | 3 | 3 | 3 | 2 | 2 | 2 | 3 | 2 |
| Potassium hydroxide, 20% aqueous solution |  |  |  |  |  | 0.3 | 0.2 | 0.1 | 0.4 | 0.3 | 0.5 |  |  |
| Hispagel ® 50 |  |  |  |  |  |  |  |  |  | 10 |  |  |  |
| Carbomer |  |  |  |  |  |  | 0.1 |  | 0.2 |  | 0.2 |  |  |
| Cosmedia ® SP |  |  |  |  | 0.15 |  |  |  |  |  |  |  |  |
| Permulen ® TR-2 Polymer |  |  |  |  |  | 0.15 |  | 0.05 |  |  |  |  |  |
| Water, perfume, preservative | q.s. | q.s. | q.s. | q.s. | q.s. | q.s. | q.s. | q.s. | q.s. | q.s. | q.s. | q.s. | q.s. |

TABLE 3

Formulations 27 to 33
(formulations for antiperspirant/deodorant use)

| Components INCI (trade name) | 27 | 28 | 29 | 30 | 31 | 32 | 33 |
|---|---|---|---|---|---|---|---|
| Emulgade ® SE-PF | 6 |  | 4.5 |  |  | 6 |  |
| Ceteareth-12 (Eumulgin ® B1) |  |  |  |  |  |  |  |
| Ceteareth-20 (Eumulgin ® B2) |  |  | 1 |  |  |  |  |
| Emulgade ® CM |  |  |  |  | 20 |  |  |
| Lameform ® TGI |  | 3 |  |  |  |  |  |
| Novata ® AB |  |  |  |  |  |  | 4 |
| Lanette ® 18 |  |  |  | 14.7 |  |  |  |
| Cutina ® HR |  |  |  | 3.7 |  |  | 6.5 |
| Dehymuls ® PGPH |  | 1 |  |  |  |  |  |
| Lanette ® E | 0.3 |  |  |  |  | 0.3 |  |
| Lanette ® 22 | 2 |  |  |  |  | 4 |  |
| Oil component from Example A | 4 | 4 | 5 | 5 | 4 | 4 | 15 |
| Cetiol ® CC |  | 3 |  |  |  |  |  |
| Cetiol ® OE | 2 |  |  | 4 |  | 3 | 9 |
| Myritol ® 331 |  |  |  |  |  |  |  |
| Cetiol ® S |  |  | 5 | 14.7 |  |  | 20 |
| Dow Corning ® 246 Fluid | 3 | 5 |  | 34 |  | 2 | 14 |
| SFE ® 839 (GE Bayer) |  | 3 |  |  |  |  |  |
| Silikonöl Wacker AK ® 350 | 1 |  |  |  |  |  |  |
| Cosmedia ® DC | 1 | 1 | 1 | 1 | 1 | 1 | 1 |
| Hydagen ® C.A.T |  |  | 2 |  |  |  |  |
| Eumulgin ® HRE 40 |  |  |  |  | 1 |  |  |
| Copherol ® 1250 C |  |  |  | 1 |  |  |  |
| Rezal ® 36 | 30 | 40 |  | 22.9 |  | 30 | 25 |
| Locron ® L |  |  | 10 |  |  |  |  |
| Hydagen ® DCMF | 0.05 |  |  |  |  |  |  |
| Glycolic Acid | 0.02 |  |  |  |  |  |  |
| Glycerin |  | 5 | 5 |  |  |  |  |
| Propylene Carbonate |  |  |  |  |  | 0.5 |  |
| Bentone ® 18 |  |  |  |  |  | 1 |  |
| Talcum |  |  |  |  | 5 | 5 |  |

TABLE 3-continued

Formulations 27 to 33
(formulations for antiperspirant/deodorant use)

| Components INCI (trade name) | 27 | 28 | 29 | 30 | 31 | 32 | 33 |
|---|---|---|---|---|---|---|---|
| MgSO4x 7H2O | | 1 | | | | | |
| Water phase II | 46.7 | | 35 | | | | |
| Water, perfume, preservative | q.s. | q.s. | q.s. | q.s. | q.s. | q.s. | q.s. |

27 - Antiperspirant/Deodorant Cream,
28 - Antiperspirant Cream (water-in-oil emulsion),
29 - Antiperspirant/Deodorant Spray,
30 - Antiperspirant stick with vitamin E,
31 - Deodorant Wipe-formulation,
32 - Antiperspirant Cream,
33 - << Soft Solid >> Antiperspirant Cream Sun protection formulations of the oil-in-water emulsion type are described in Table 4; emulsions for personal (skin) care are described in Table 5. Through the use of the oil component according to the invention, sensory behavior on application is positively influenced. The quantities shown are based on %, by weight, of the commercially-available substances in the composition as a whole.

TABLE 4

Oil-in-water sun protection emulsions

| Component | 1 | 2 | 3 | 4 | 5 | 6 | 7 | 8 | 9 | 10 | 11 |
|---|---|---|---|---|---|---|---|---|---|---|---|
| L = Lotion, C = Cream, S = spray | L | C | L | C | L | C | S | C | C | L | L |
| Eumulgin ® VL 75 | 2 | | | | 3 | | | | 1 | | |
| Eumulgin ® B2 | | | | 2 | | | | | | 1 | |
| Tween ® 60 | | | | | | | | | | 1 | |
| Cutina ® E 24 | | | | | 0.5 | | | | | | |
| Hostaphat ® KL 340 N | | | | | | | | | | | 0.5 |
| Eumulgin ® SG | | | 0.5 | | | 0.5 | | 0.3 | 0.1 | | |
| Lanette ® E | | | | | | | | 0.1 | 0.5 | | |
| Amphisol ® K | 0.5 | | | | | | | 1 | | | |
| Sodium stearate | | | | | 1 | | | | | | |
| Emulgade ® PL 68/50 | | 2 | 1 | | | 3 | | | | | |
| Tego ® Care 450 | | 2 | | | | | | | 2 | | |
| Cutina ® MD | | | | 2 | 1 | 3 | 4 | | | | 1 |
| Lanette ® 14 | | 1 | | | | | | | | | |
| Lanette ® O | | | | 2 | | | | 2 | 1 | 1 | |
| Cutina ® PES | 1 | 1 | | 2 | | | | | | 1 | |
| Allianz ® OPT | 1 | | | 1 | 1 | | | 2 | | | 2 |
| Cosmedia ® DC | | 1.5 | 2 | | | 1.5 | 2 | | 1.5 | 1.5 | |
| Emery ® 1780 | | | | 1 | 1 | | | | | | |
| Lanolin, anhydrous, USP | | | | | | 1 | 1 | | | | |
| Oil component from Example A | 6 | 2 | 4 | 7 | 3 | 7 | 6 | 6 | 4 | 4 | 5 |
| Myritol ® PC | | | | | | | | | 5 | | |
| Myritol ® 331 | 6 | | 4 | | | 5 | 8 | | | 10 | 8 |
| Finsolv ® TN | | | | | 5 | | | 3 | 3 | | |
| Cetiol ® CC | 6 | | 6 | | | 5 | 5 | | | | |
| Cetiol ® OE | | | | | 2 | | | | | | 2 |
| Dow Corning DC ® 244 | | 2 | | | 1 | | | | | | |
| Dow Corning DC ® 2502 | | 1 | | | 1 | | | 3 | | | |
| Ceraphyl ® 45 | | | | | | | | | | 2 | 2 |
| Silikonöl Wacker AK ® 350 | | | | | 1 | | | | | | |
| Cetiol ® 868 | | 2 | | | | | | | | | |
| Cetiol ® J 600 | | 2 | | | | | | | | | |
| Mineral oil | | | | | 5 | | | | | | |
| Cetiol ® B | 4 | | 4 | | | | | 4 | | | |
| Eutanol ® G | | 3 | | | | 3 | | | | | |
| Eutanol ® G 16 S | 3 | | | | | | | | | | |
| Cetiol ® PGL | | | | | | | | | | 2 | |
| Photonyl ® LS | | | | | | | | | | 2 | |
| Panthenol | | | | | | | 1 | | | | |
| Bisabolol | | | | | | | 0.2 | | | | |
| Tocopherol/Tocopherylacetate | | | | | | | 1 | | | | |
| Neo Heliopan ® Hydro (Na salt) | | | | | | | | | | 3 | |
| Eusolex ® OCR | 6 | | 9 | | 5 | 7 | 9 | | 4 | | 7 |
| Neo Heliopan AP (Na salt) | | | | 0.5 | | 1 | | | | | |
| Neo Heliopan ® BB | | | | | | | | 1 | 1 | | 1 |
| Neo Heliopan ® MBC | | 2 | | 1 | | | | 3 | 1 | | 3 |
| Neo Heliopan ® OS | 2 | | | | | | | | 7 | | |
| Neo Heliopan ® E 1000 | | 4 | | | | | | 5 | | | |
| Neo Heliopan ® AV | | 4 | 7.5 | 5 | | 7.5 | 4 | 5 | 4 | 7.5 | |
| Uvinul ® A PLUS | | | | | | 1 | 2 | | | | |

TABLE 4-continued

Oil-in-water sun protection emulsions

| Component | 1 | 2 | 3 | 4 | 5 | 6 | 7 | 8 | 9 | 10 | 11 |
|---|---|---|---|---|---|---|---|---|---|---|---|
| Uvinul ® T 150 | 1 | | | | | | | | 1.3 | 1 | 1 |
| Tinosorb ® M | | 2 | | | | 2 | 2 | | | | |
| Tinosorb ® S | | | 1 | | | 2 | 2 | | | | |
| Parsol ® 1789 | 1 | | | | | | | | 2 | | 1 |
| Z-Cote ® HP 1 | 7 | 2 | 5 | | | 7 | 5 | | 6 | 2 | |
| Eusolex ® T 2000 | 5 | 2 | | | 10 | | | 10 | | 2 | |
| Veegum ® Ultra | 1.5 | | 1.5 | | | 1.5 | 1.2 | | 1 | | |
| Keltrol ® T | 0.5 | | 0.5 | | | 0.5 | 0.4 | | 0.5 | | |
| Cosmedia ® SP | | | 0.2 | 0.3 | | | 0.1 | | | 0.2 | |
| Pemulen ® TR 2 | | 0.3 | | 0.3 | | | | 0.2 | | | 0.3 |
| Ethanol | | 5 | | 8 | | | | | | | |
| Butylene glycol | 1 | | 3 | 3 | | | | | 8 | 1 | |
| Glycerin | 2 | 4 | 3 | 3 | | 3 | 3 | 3 | 5 | | 3 |
| Preservative, NaOH | | | | | q.s. to 100 | | | | | | |
| Water | | | | | | | | | | | |

TABLE 5

Oil-in-water emulsions for personal (skin) care

| Component | 12 | 13 | 14 | 15 | 16 | 17 | 18 | 19 | 20 | 21 | 22 |
|---|---|---|---|---|---|---|---|---|---|---|---|
| L = Lotion, C = Cream | C | C | L | C | L | C | L | L | L | L | C |
| Eumulgin ® VL 75 | | | 5 | | 4 | | | | | | 2 |
| Generol ® R | | | | | | 2 | | | | | |
| Eumulgin ® B2 | | | | | | | | 1 | | | |
| Tween ® 60 | | | | | | | | 1 | | | |
| Cutina ® E 24 | | | | 0.5 | | | | | | | |
| Eumulgin ® SG | | | 0.1 | 0.5 | | 0.4 | | 0.2 | 0.1 | | |
| Lanette ® E | 0.5 | | | | | | | | | | |
| Amphisol ® K | 0.5 | 0.5 | | | | | | | | | |
| Sodium stearate | | | | | 1 | | | | | | |
| Emulgade ® PL 68/50 | | 2 | | 2 | | | | 3 | 4 | | |
| Tego ® Care 450 | | 1 | | | | | | 1 | | | |
| Cutina ® MD | 2 | 1 | 1 | 1 | | 5 | | | | 2 | |
| Lanette ® 14 | | | | | 1 | | 2 | | | 1 | |
| Lanette ® O | 2 | | | 2 | 1 | 3 | 1 | | 1 | 1 | 3 |
| Cutina ® PES | 1 | 2 | | 3 | 1 | | | | | | 3 |
| Novata ® AB | | | | | | | | 1 | 1 | | |
| Emery ® 1780 | | | | | | | | | | | 0.5 |
| Lanolin, anhydrous, USP | | | | | | 4 | | | | | |
| Cosmedia ® DC | | | 2 | | | 1.5 | | 1 | 1 | | |
| Cetiol ® SB 45 | | | | | | | 2 | | | | |
| Cegesoft ® C 17 | 2 | | | | | | | | | | |
| Oil component from Example A | 5 | 5 | 4 | 4 | 3 | 4 | 5 | 4 | 5 | 10 | 2 |
| Myritol ® PC | 6 | | | | 5 | | | | | | |
| Myritol ® 331 | 2 | 5 | | | | | 2 | | | | 3 |
| Finsolv ® TN | | | 3 | 5 | | | 3 | 3 | | 1 | |
| Cetiol ® CC | | | 3 | | | 4 | 3 | | | | |
| Cetiol ® OE | | | 2 | | | 2 | | 5 | | | |
| Dow Corning DC ® 245 | | 2 | | 1 | 4 | | | | | 8 | 2 |
| Dow Corning DC ® 2502 | | 1 | | 1 | | | | | | | 3 |
| Prisorine ® 3758 | 3 | | | | | | | | | 2 | |
| Silikonöl Wacker AK ® 350 | | | | 1 | | | | | | | 2 |
| Cetiol ® 868 | | 2 | | | | | | | | | |
| Cetiol ® J 600 | | 2 | 2 | | | | | | | | |
| Ceraphyl ® 45 | | | | | 3 | | | | | | |
| Cetiol ® SN | | | 5 | | | | | | | | |
| Cetiol ® B | | 5 | | | 5 | | 4 | | | 3 | |
| Eutanol ® G | 3 | 5 | | 5 | | | | | | | |
| Cetiol ® PGL | | | | | | | 5 | 2 | | | |
| Dry Flo ® Plus | 1 | | | | | | | | | | 1 |
| SFE 839 | 1 | 1 | | | | | | | | | |
| Almond oil | | | | | 2 | | | | | | |
| Photonyl ® LS | | | | | 2 | | | | | | |
| Panthenol | | | | | 1 | | | | | | |
| Bisabolol | | | | | | 0.2 | | | | | |
| Tocopherol/ Tocopherylacetate | | | | | | | 1 | | | | |
| Veegum ® ultra | | | | | | | | | 1 | | |
| Keltrol ® T | | | | | | | | | 0.5 | | |
| Cosmedia ® SP | 0.5 | | | | | 0.5 | 0.5 | 0.2 | | | 0.5 |
| Carbopol ® ETD 2001 | | 0.3 | | 0.3 | | | | | | | |
| Pemulen ® TR 2 | | | 0.3 | | | 0.3 | | | | | |
| Ethanol | | 5 | | 8 | | | | | | | 10 |
| Butylene glycol | 5 | | 2 | 3 | 3 | | | | | 8 | |
| Glycerin | 2 | 4 | 3 | 3 | | 7 | 5 | 3 | 5 | | |
| Water, preservative, NaOH | | | | | to 100, q.s., pH 6.5-7.5 | | | | | | |

Sun Protection and Skin Care Formulations of the Water-in-Oil Type

Sun protection formulations of the w/o emulsion type are described in Table 6; emulsions for personal (skin) care are described in Table 7. Through the use of the oil component according to the invention, sensory behavior on application is positively influenced. The quantities shown are based on %, by weight, of the commercially-available substances in the composition as a whole.

TABLE 6

Water-in-oil sun protection formulations

| Component | 23 | 24 | 25 | 26 | 27 | 28 | 29 | 30 | 31 | 32 | 33 |
|---|---|---|---|---|---|---|---|---|---|---|---|
| L = Lotion; C = Cream | C | L | C | L | C | L | L | L | L | C | C |
| Dehymuls ® PGPH | 4 | 2 | 1 | 3 | 3 | 1 | 1 | 2 | 2 | 4 | 1 |
| Monomuls ® 90-O18 | | | 2 | | | | | | | | |
| Lameform ® TGI | 2 | | 4 | | 3 | | | | | 1 | 3 |
| Abil ® EM 90 | | | | | | 4 | | | | | |
| Isolan ® PDI | | | | | | | 4 | 2 | | | |
| Zinc stearate | 1 | | | 1 | 1 | | | | 1 | 1 | |
| Beeswax | 1 | | 5 | 1 | | | | 5 | | 7 | 5 |
| Tego ® Care CG | | | | | 1 | | 1 | | | | 0.5 |
| Prisorine ® 3505 | | 1 | | | | 1 | 1 | | | | 1 |
| Cosmedia DC | 3 | 4 | 2 | 1 | 1 | 2 | 2 | 2 | 3 | 1 | 1 |
| Oil component from Example A | 5 | 4 | 4 | 3 | 2 | 4 | 3 | 4 | 2 | 3 | 5 |
| Myritol ® 331 | 2 | | | | 3 | 6 | | | | | 3 |
| Finsolv ® TN | | | 5 | | | | 2 | | | | |

TABLE 6-continued

Water-in-oil sun protection formulations

| Component | 23 | 24 | 25 | 26 | 27 | 28 | 29 | 30 | 31 | 32 | 33 |
|---|---|---|---|---|---|---|---|---|---|---|---|
| Cetiol ® CC | 5 |  | 2 |  | 4 | 2 |  |  | 2 | 3 | 5 |
| Tegosoft DEC |  | 4 |  | 3 |  |  | 5 | 5 |  |  |  |
| Cetiol ® OE |  |  |  |  | 4 |  | 5 |  | 4 | 2 |  |
| Dow Corning DC ® 244 |  |  | 3 |  |  | 2 |  | 2 | 4 |  |  |
| Dow Corning DC ® 2502 | 1 |  | 1 |  | 2 | 1 |  |  |  |  | 1 |
| Silikonöl Wacker AK ® 350 |  | 1 |  | 4 |  |  |  | 3 |  |  |  |
| Cetiol ® PGL |  | 3 |  |  |  | 2 |  |  | 4 |  |  |
| Copherol ® F 1300 |  |  |  |  |  | 1 |  |  |  |  |  |
| Magnesium sulfate x 7 H$_2$O |  |  |  |  |  | 1 |  |  |  |  |  |
| Neo Heliopan ® Hydro (Na salt) | 2 |  | 2.2 |  | 3 | 3 |  |  | 1 |  | 2 |
| Neo Heliopan ® 303 |  | 5 |  |  | 4 |  |  |  | 4 | 4 |  |
| Uvasorb ® HEB | 1 |  |  | 1 | 1 |  |  |  |  |  | 2 |
| Neo Heliopan ® MBC | 2 |  |  |  |  | 2 | 2 | 2 |  |  |  |
| Uvinul ® A plus |  |  |  |  |  | 2 |  |  |  | 3 | 3 |
| Neo Heliopan ® AP (Na salt) |  | 2 | 2 |  | 1 |  |  |  |  | 1 | 6 |
| Neo Heliopan ® AV | 3 |  | 4 | 6 | 4 | 7.5 | 4 | 5 | 5 |  | 1 |
| Uvinul ® T 150 | 1 | 1 |  |  |  | 2.5 |  | 1 |  |  |  |
| Parsol ® 1789 | 2 | 1 |  |  |  |  | 2 |  | 2 | 2 |  |
| Zinc oxide NDM |  |  |  |  |  |  | 10 |  | 3 |  | 4 |
| Tinosorb ® M |  |  | 3 |  | 3 |  |  | 2 |  | 2 |  |
| Tinosorb ® S |  |  | 3 |  | 3 |  |  | 2 |  | 2 |  |
| Eusolex ® T Aqua |  |  |  | 8 |  |  |  | 5 |  |  |  |
| Eusolex ® T 2000 |  |  |  |  |  | 5 |  | 3 | 3 |  | 4 |
| Ethanol |  |  |  |  |  |  |  |  |  | 8 |  |
| Glycerin | 5 | 3 | 3 | 3 | 5 | 3 | 2 | 3 | 10 | 4 | 3 |
| Water, preservative | to 100, q.s. |||||||||||

TABLE 7

Water-in-oil emulsions for personal (skin) care

| Component | 34 | 35 | 36 | 37 | 38 | 39 | 40 | 41 | 42 | 43 | 44 |
|---|---|---|---|---|---|---|---|---|---|---|---|
| L = Lotion, C = Cream | C | L | C | L | C | L | L | L | C | C | C |
| Dehymuls ® PGPH | 1 | 3 | 1 | 2 | 3 | 1 | 1 | 2 | 1 | 1 | 1 |
| Monomuls ® 90-O18 | 2 |  |  |  |  |  |  |  | 2 |  | 2 |
| Lameform ® TGI | 4 | 1 |  |  | 3 |  |  | 1 | 4 | 3 | 3 |
| Abil ® EM 90 |  |  |  |  |  |  | 4 |  |  |  |  |
| Isolan ® PDI |  |  |  |  |  | 4 |  |  |  |  |  |
| Glucate ® DO |  |  |  | 5 |  |  |  |  |  |  |  |
| Arlacel ® 83 |  |  | 5 |  |  |  |  |  |  |  |  |
| Dehymuls ® FCE |  |  |  |  |  |  |  |  |  |  |  |
| Dehymuls ® HRE 7 |  |  |  |  |  |  |  | 4 |  | 1 |  |
| Zinc stearate | 2 | 1 |  | 1 | 1 |  |  | 1 | 1 | 1 |  |
| Microcrystalline wax |  |  | 5 |  |  | 2 |  |  |  |  | 5 |
| Beeswax | 4 |  |  | 1 |  |  |  | 1 | 4 | 7 |  |
| Tego Care ® CG |  |  |  |  | 1 |  |  |  |  |  | 0.5 |
| Prisorine ® 3505 |  |  | 1 | 1 |  | 1 | 1 |  |  |  | 1 |
| Dry Flo ® Plus |  |  |  |  |  |  |  |  |  |  |  |
| SFE 839 |  |  |  |  |  | 3 |  |  |  |  |  |
| Emery ® 1780 | 1 |  |  |  |  |  |  |  |  | 4 | 1 |
| Lanolin; anhydrous USP |  |  | 5 |  |  |  |  |  |  | 4 |  |
| Oil component from Example A | 3 | 4 | 2 | 12 | 10 | 2 | 2 | 6 | 3 | 12 | 1 |
| Cegesoft ® C 17 |  |  | 3 |  |  |  |  |  |  | 1 |  |
| Myritol ® PC |  |  |  |  |  | 2 |  | 4 |  |  |  |
| Myritol ® 331 | 6 |  |  |  | 2 | 6 | 2 |  |  |  | 8 |
| Finsolv ® TN |  |  |  | 5 |  |  | 2 | 5 |  |  |  |
| Cetiol ® A |  | 6 |  |  |  | 4 |  |  |  |  |  |
| Cetiol ® CC |  | 8 |  |  | 2 | 2 | 2 |  |  |  | 5 |
| Cetiol ® SN |  | 5 |  |  |  |  |  | 3 |  |  |  |
| Cetiol ® OE | 3 |  |  |  | 4 |  | 2 |  | 4 | 2 |  |
| Dow Corning DC ® 244 |  |  |  |  | 1 |  | 2 |  |  |  |  |
| Dow Corning DC ® 2502 |  |  | 1 |  | 2 |  |  |  |  |  |  |
| Prisorine ® 3758 |  |  |  |  | 3 |  |  |  |  |  |  |
| Silikonöl Wacker AK ® 350 |  |  |  |  | 4 |  |  | 3 |  |  |  |
| Cetiol ® 868 |  |  |  |  |  |  |  |  |  | 2 | 7 |
| Cetiol ® J 600 |  |  | 4 |  |  | 2 |  |  |  |  |  |
| Ceraphyl ® 45 |  |  |  |  | 2 |  |  | 2 |  | 6 |  |
| Mineral oil |  |  |  |  |  | 4 |  |  |  |  |  |
| Cetiol ® B |  |  | 2 | 4 |  |  |  |  |  | 3 |  |
| Eutanol ® G 16 |  | 1 |  |  |  |  |  |  |  | 3 |  |
| Eutanol ® G |  |  | 3 |  |  |  |  | 8 |  |  |  |
| Cetiol ® PGL |  |  |  |  |  | 4 |  |  | 9 |  |  |
| Almond oil |  |  |  |  | 1 |  | 5 |  |  |  |  |
| Insect Repellent ® 3535 | 2 |  |  |  |  |  |  |  |  |  |  |
| N,N-Diethyl-m-toluamide |  |  |  |  | 3 |  |  | 5 |  |  |  |
| Photonyl ® LS | 2 | 2 |  |  |  |  |  |  |  |  |  |
| Panthenol |  |  |  |  |  |  | 1.0 |  |  |  |  |
| Bisabolol |  |  |  |  |  |  | 0.2 |  |  |  |  |
| Tocopherol/Tocopheryl Acetate |  |  |  |  |  |  | 1.0 |  |  |  |  |
| Magnesium sulfate x 7 water |  |  |  |  |  |  |  |  | 1 |  |  |
| Bentone ® 38 |  |  |  |  |  | 1 |  |  |  |  |  |

TABLE 7-continued

Water-in-oil emulsions for personal (skin) care

| Component | 34 | 35 | 36 | 37 | 38 | 39 | 40 | 41 | 42 | 43 | 44 |
|---|---|---|---|---|---|---|---|---|---|---|---|
| Propylene carbonate | | | | | 0.5 | | | | | | |
| Ethanol | | | | | | | | | | 8 | |
| Butylene Glycol | | | 2 | 6 | | | 2 | 5 | | | 2 |
| Glycerin | 5 | 3 | 3 | | 5 | 3 | 2 | | 10 | 4 | |
| Water, preservative | | | | | to 100, q.s. | | | | | | |

Product/Trademark Guide

1) Abil ® EM 90
   INCI: Cetyl Dimethicone Copolyol
   Manufacturer: Tego Cosmetics (Goldschmidt)
2) Allianz ® OPT
   INCI: Acrylates/C12-22 Alkyl Methacrylate Copolymer
   Manufacturer: Rohm and Haas
3) Amphisol ® K
   INCI: Potassium Cetyl Phosphate
   Manufacturer: Hoffmann La Roche
4) Antaron ® V 220
   INCI: PVP/Eicosene Copolymer
   Manufacturer: GAF General Aniline Firm Corp. (IPS-Global)
5) Antaron ® V 216
   INCI: PVP/Hexadecene Copolymer
   Manufacturer: GAF General Aniline Firm Corp. (IPS-Global)
6) Arlacel ® 83
   INCI: Sorbitan Sesquioleate
   Manufacturer: Uniqema (ICI Surfacants)
7) Arlacel ® P 135
   INCI: PEG-30 Dipolyhydroxystearate
   Manufacturer: Uniqema (ICI Surfacants)
8) Bentone ® 38
   INCI: Quaternium-18 Hectorite
   Manufacturer: Rheox (Elementis Specialties)
9) Carbopol ® 980
   INCI: Carbomer
   Manufacturer: Goodrich
10) Carbopol ® 2984
    INCI: Carbomer
    Manufacturer: Noveon, Inc.
11) Carbopol ® ETD 2001
    INCI: Carbomer
    Manufacturer: Noveon, Inc.
12) Carbopol ® Ultrez 10
    INCI: Carbomer
    Manufacturer: Noveon, Inc.
13) Cegesoft ® C 17
    INCI: Myristyl Lactate
    Manufacturer: Cognis GmbH, Grunau
14) Cegesoft ® PFO
    INCI: *Passiflora Incamata* (EU)
    Manufacturer: Cognis GmbH
15) Cegesoft ® PS 6
    INCI: Olus
    Manufacturer: Cognis GmbH
16) Ceraphyl ® 45
    INCI: Diethylhexyl Malate
    Manufacturer: International Specialty Products
17) Cetiol ® 868
    INCI: Ethylhexyl Stearate
    Manufacturer: Cognis GmbH
18) Cetiol ® A
    INCI: Hexyl Laurate
    Manufacturer: Cognis GmbH
19) Cetiol ® B
    INCI: Dibutyl Adipate
    Manufacturer: Cognis GmbH
20) Cetiol ® CC
    INCI: Dicaprylyl Carbonate
    Manufacturer: Cognis GmbH
21) Cetiol ® J 600
    INCI: Oleyl Erucate
    Manufacturer: Cognis GmbH
22) Cetiol ® LC
    INCI: Coco-Caprylate/Caprate
    Manufacturer: Cognis GmbH
23) Cetiol ® OE
    INCI: Dicaprylyl Ether
    Manufacturer: Cognis GmbH
24) Cetiol ® PGL
    INCI: Hexyldecanol, Hexyldecyl Laurate
    Manufacturer: Cognis GmbH
25) Cetiol ® S
    INCI: Diethylhexylcyclohexane
    Manufacturer: Cognis GmbH
26) Cetiol ® SB 45
    INCI: Shea Butter *Butyrospermum Parkii* (Linne)
    Manufacturer: Cognis GmbH
27) Cetiol ® SN
    INCI: Cetearyl Isononanoate
    Manufacturer: Cognis GmbH
28) Copherol ® F 1300 C
    INCI: Tocopherol
    Manufacturer: Cognis GmbH
29) Copherol 1250 C
    INCI: Tocopheryl Acetate
    Manufacturer: Cognis GmbH
30) Cosmedia ® DC
    INCI: Hydrogenated Dimer Dilinoleyl/Dimethylcarbonate Copolymer
    Manufacturer: Cognis GmbH
31) Cosmedia ® SP
    INCI: Sodium Polyacrylate
    Manufacturer: Cognis GmbH
32) Cutina ® E 24
    INCI: PEG-20 Glyceryl Stearate
    Manufacturer: Cognis GmbH
33) Cutina ® HR
    INCI: Hydrogenated Castor Oil
    Manufacturer: Cognis GmbH
34) Cutina ® MD
    INCI: Glyceryl Stearate
    Manufacturer: Cognis GmbH
35) Cuitina ® PES
    INCI: Pentaerythrityl Distearate
    Manufacturer: Cognis GmbH
36) Dehymuls ® FCE
    INCI: Dicocoyl Pentaerythrityl Distearyl Citrate
    Manufacturer: Cognis GmbH
37) Dehymuls ® HRE 7
    INCI: PEG-7 Hydrogenated Castor Oil
    Manufacturer: Cognis GmbH
38) Dehymuls ® PGPH
    INCI: Polyglyceryl-2 Dipolyhydroxystearate
    Manufacturer: Cognis GmbH

| Product/Trademark Guide |
| --- |
| 39) Dow Corning ® 244 Fluid<br>INCI: Cyclomethicone<br>Manufacturer: Dow Corning |
| 40) Dow Corning ® 246 Fluid<br>INCI: Cyclopentasiloxane<br>Manufacturer: Dow Corning |
| 41) Dow Corning ® 2502<br>INCI: Cetyl Dimethicone<br>Manufacturer: Dow Corning |
| 42) Dry ® Flo Plus<br>INCI: Aluminium Starch Octenylsuccinate<br>Manufacturer: National Starch |
| 43) Elfacos ® ST 37<br>INCI: PEG-22 Dodecyl Glycol Copolymer<br>Manufacturer: Akzo-Nobel |
| 44) Elfacos ® ST 9<br>INCI: PEG-45 Dodecyl Glycol Copolymer<br>Manufacturer: Akzo-Nobel |
| 45) Emery ® 1780<br>INCI: Lanolin Alcohol<br>Manufacturer: Cognis Corporation |
| 46) Emulgade ® CM<br>INCI: Cetearyl Isononanoate and Ceteareth-20 and Cetearyl Alcohol and Glyceryl Stearate and Glycerin and Ceteareth-12 and Cetyl Palmitate<br>Manufacturer: Cognis GmbH |
| 47) Emulgade ® PL 68/50<br>INCI: Cetearyl Glucoside, Cetearyl Alcohol<br>Manufacturer: Cognis GmbH |
| 48) Emulgade ® SE-PF<br>INCI: Glyceryl Stearate (and) Ceteareth-20 (and) Ceteareth-12 (and) Cetearyl Alcohol (and) Cetyl Palmitate<br>Manufacturer: Cognis GmbH |
| 49) Eumulgin ® B1<br>INCI: Ceteareth-12<br>Manufacturer: Cognis GmbH |
| 50) Eumulgin ® B 2<br>INCI: Ceteareth-20<br>Manufacturer: Cognis GmbH |
| 51) Eumulgin ® HRE 40<br>INCI: PEG-40 Hydrogenated Castor Oil<br>Manufacturer: Cognis GmbH |
| 52) Eumulgin ® SG<br>INCI: Sodium Stearoyl Glutamate<br>Manufacturer: Cognis GmbH |
| 53) Eumulgin ® VL 75<br>INCI: Lauryl Glucoside (and) Polyglyceryl-2 Dipolyhydroxystearate (and) Glycerin<br>Manufacturer: Cognis GmbH |
| 54) Eusolex ® OCR<br>INCI: Octocrylene<br>Manufacturer: Merck |
| 55) Eusolex ® T 2000<br>INCI: Titanium Dioxide, Alumina, Simethicone<br>Manufacturer: Merck |
| 56) Eusolex ® T AQUA<br>INCI: Water and Titanium Dioxide and Alumina and Sodium Metaphosphate and Phenoxyethanol and Sodium Methylparaben<br>Manufacturer: Merck |
| 57) Eutanol ® G<br>INCI: Octyldodecanol<br>Manufacturer: Cognis GmbH |
| 58) Eutanol ® G 16<br>INCI: Hexyldecanol<br>Manufacturer: Cognis GmbH |
| 59) Eutanol ® G 16 S<br>INCI: Hexyldecyl Stearate<br>Manufacturer: Cognis GmbH |
| 60) Finsolv ® TN<br>INCI: C 12/15 Alkyl Benzoate<br>Manufacturer: Findex (Nordmann/Rassmann) |
| 61) Generol ® R<br>INCI: *Brassica Campestris* (Rapseed) Sterols<br>Manufacturer: Cognis GmbH |
| 62) Glucate ® DO<br>INCI: Methyl Glucose Dioleate<br>Manufacturer: NRC Nordmann/Rassmann |
| 63) Hispagel ® 200<br>INCI: Glycerin, Glyceryl Polyacrylate<br>Manufacturer: Cognis GmbH |
| 64) Hostaphat ® KL 340 N<br>INCI: Trilaureth-4 Phosphate<br>Manufacturer: Clariant |
| 65) Hydagen ® C.A.T.<br>INCI Triethyl Citrate<br>Manufacturer: Cognis GmbH |
| 66) Hydagen ® DCMF<br>INCI: Chitosan<br>Manufacturer: Cognis GmbH |
| 67) Insect Repellent ® 3535<br>INCI: Ethyl Butylacetylaminopropionate<br>Manufacturer: EMD Chemicals Inc |
| 68) Isolan ® PDI<br>INCI: Diisostearoyl Polyglyceryl-3 Diisostearate<br>Manufacturer: Goldschmidt AG |
| 69) Keltrol ® T<br>INCI: Xanthan Gum<br>Manufacturer: CP Kelco |
| 70) Lameform ® TGI<br>INCI: Polyglyceryl-3 Diisostearate<br>Manufacturer: Cognis GmbH |
| 71) Lanette ® 14<br>INCI: Myristyl Alcohol<br>Manufacturer: Cognis GmbH |
| 72) Lanette 18<br>INCI: Stearyl Alcohol<br>Manufacturer: Cognis GmbH |
| 73) Lanette ® 22<br>INCI: Behenyl Alcohol<br>Manufacturer: Cognis GmbH |
| 74) Lanette ® E<br>INCI: Sodium Cetearyl Sulfate<br>Manufacturer: Cognis GmbH |
| 75) Lanette ® O<br>INCI: Cetearyl Alcohol<br>Manufacturer: Cognis GmbH |
| 76) Locron ® L<br>INCI: Aluminium Chlorhydrate<br>Manufacturer: Clariant |
| 77) Lucentite ® SAN<br>INCI: Quaternium-18 Hectoritr<br>Manufacturer: Co-Op Chemical Co., Ltd. |
| 78) Monomuls ® 90-O 18<br>INCI: Glyceryl Oleate<br>Manufacturer: Cognis GmbH |
| 79) Myrj ® 51<br>INCI: PEG-30-Sterate<br>Manufacturer: Uniqema |
| 80) Myritol ® 312<br>INCI: Caprylic/Capric Triglyceride<br>Manufacturer: Cognis GmbH |
| 81) Myritol ® 331<br>INCI: Cocoglycerides<br>Manufacturer: Cognis GmbH |
| 82) Myritol ® PC<br>INCI: Propylene Glycol Dicaprylate/Dicaprate<br>Manufacturer: Cognis GmbH |
| 83) Neo Heliopan ® 303<br>INCI: Octocrylene<br>Manufacturer: Symrise |

| Product/Trademark Guide |
|---|
| 84) Neo Heliopan ® AP<br>INCI: Disodium Phenyl Dibenzimidazole Tetrasulfonate<br>Manufacturer: Symrise |
| 85) Neo Heliopa ® AV<br>INCI: Ethylhexyl Methoxycinnamate<br>Manufacturer: Symrise |
| 86) Neo Heliopan ® BB<br>INCI: Benzophenone-3<br>Manufacturer: Symrise |
| 87) Neo Heliopan ® E 1000<br>INCI: Isoamyl-p-Methoxycinnamate<br>Manufacturer: Symrise |
| 88) Neo Heliopan ® Hydro<br>INCI: Phenylbenzimidazole Sulfonic Acid<br>Manufacturer: Symrise |
| 89) Neo Heliopan ® MBC<br>INCI: 4-Methylbenzylidene Camphor<br>Manufacturer: Symrise |
| 90) Neo Heliopan ® OS<br>INCI: Ethylhexyl Salicylate<br>Manufacturer: Symrise |
| 91) Novata ® AB<br>INCI: Cocoglycerides<br>Manufacturer: Cognis GmbH |
| 92) Parsol ® 1789<br>INCI: Butyl Methoxydibenzoylmethane<br>Manufacturer: Hoffmann-La Roche (Givaudan) |
| 93) Pemulen ® TR-2 Polymer<br>INCI: Acrylates/C10-30 Alkylacrylate Crosspolymer<br>Manufacturer: Noveon, Inc. |
| 94) Photonyl ® LS<br>INCI: Arginine, Disodium Adenosine Triphosphate, Mannitol, Pyridoxine HCL, Phenylalanine, Tyrosine<br>Manufacturer: Laboratoires Serobiologiques (Cognis) |
| 95) Prisorine ® 3505<br>INCI: Isostearic Acid<br>Manufacturer: Uniqema |
| 96) Prisorine ® 3758<br>INCI: Hydrogenated Polyisobutene<br>Manufacturer: Uniqema |
| 97) Rezal 36G<br>INCI: Aluminum Zirconium Tetrachlorohydrex GLY<br>Manufacturer: Reheis, Inc. |
| 98) SFE ® 839<br>INCI: Cyclopentasiloxane and Dimethicone/Vinyl Dimethicone Crosspolymer<br>Manufacturer: GE Silicones |
| 99) Silikonol Wacker AK ® 350<br>INCI: Dimethicone<br>Manufacturer: Wacker |
| 100) Tego ® Care 450<br>INCI: Polyglyceryl-3 Methylglucose Distearate<br>Manufacturer: Tego Cosmetics (Goldschmidt) |
| 101) Tego ® Care CG 90<br>INCI: Cetearyl Glucoside<br>Manufacturer: Goldschmidt |
| 102) Tegosoft ® DEC<br>INCI: Diethylhexyl Carbonate<br>Manufacturer: Goldschmidt |
| 103) Tinosorb ® S<br>INCI: Bis-Ethylhexyloxyphenol Methoxyphenyl Triazine<br>Manufacturer: Ciba Specialty Chemicals Corporation |
| 104) Tinosorb ® M<br>INCI: Methylene Bis-Benzotriazolyl Tetramethylbutylphenol<br>Herstelller: Ciba Specialty Chemicals Corporation |
| 105) Tween ® 60<br>INCI: Polysorbate 60<br>Manufacturer: Uniqema (ICI Surfactants) |
| 106) Uvasorb ® HEB<br>INCI: Diethylhexyl Butamido Triazone<br>Manufacturer: 3V Inc. |
| 107) Unirep ® U-18<br>INCI: Dimethyl Phthalate and Diethyl Toluamide and Ethyl Hexanediol<br>Manufacturer: Induchem AG |
| 108) Uvinul ® T 150<br>INCI: Ethylhexyl Triazone<br>Manufacturer: BASF |
| 109) Uvinul ® A plus<br>INCI: Diethylamino Hydroxybenzoyl Hexyl Benzoate<br>Manufacturer: BASF |
| 110) Veegum ® Ultra<br>INCI: Magnesium Aluminium Silicate<br>Manufacturer: R. T. Vanderbilt Company, Inc. |
| 111) Veegum ® Plus<br>INCI: Magnesium Aluminum Silicate and Cellulose Gum<br>Manufacturer: R. T. Vanderbilt Company, Inc. |
| 112) Z-Cote ® HP 1<br>INCI: Zinc Oxide and Triethoxycaprylylsilane<br>Manufacturer: BASF |
| 113) Zinc Oxide NDM<br>INCI: Zinc Oxide<br>Manufacturer: Symrise |

The invention claimed is:

1. A fatty acid ester mixture of 2-ethylhexanol and fatty acids, comprising 2-ethylhexyl fatty acid esters, wherein the aggregate amount of $C_{12}$ and $C_{14}$ 2-ethylhexyl fatty acid esters is 85% or more, based on the total weight of all fatty acid esters in the mixture.

2. The fatty acid ester mixture according to claim 1, wherein the aggregate amount of $C_{12}$ and $C_{14}$ 2-ethylhexyl fatty acid esters is 90% or more, based on the total weight of all fatty acid esters in the mixture.

3. The fatty acid ester mixture according to claim 1, wherein the aggregate amount of $C_{12}$ and $C_{14}$ 2-ethylhexyl fatty acid esters is 95% or more, based on the total weight of all fatty acid esters in the mixture.

4. The fatty acid ester mixture according to claim 1, wherein the aggregate amount of 2-ethylhexyl fatty acid esters with a carbon chain length of 10 or less is 3% or less, based on the total weight of all fatty acid esters in the mixture.

5. The fatty acid ester mixture according to claim 1, wherein the aggregate amount of 2-ethylhexyl fatty acid esters with a carbon chain length of 10 or less is 2% or less, based on the total weight of all fatty acid esters in the mixture.

6. The fatty acid ester mixture according to claim 1, wherein the aggregate amount of 2-ethylhexyl fatty acid esters with a carbon chain length of 10 or less is 1.5% or less, based on the total weight of all fatty acid esters in the mixture.

7. The fatty acid ester mixture according to claim 1, wherein the aggregate amount of 2-ethylhexyl fatty acid esters with a carbon chain length of 16 or more is 8% or less, based on the total weight of all fatty acid esters in the mixture.

8. The fatty acid ester mixture according to claim 1, wherein the aggregate amount of 2-ethylhexyl fatty acid esters with a carbon chain length of 16 or more is 4% or less, based on the total weight of all fatty acid esters in the mixture.

9. The fatty acid ester mixture according to claim 1, wherein the aggregate amount of 2-ethylhexyl fatty acid esters with a carbon chain length at 16 or more is 3% or less, based on the total weight of all fatty acid esters in the mixture.

10. The fatty acid ester mixture according to claim 1, wherein the aggregate amount of 2-ethylhexyl fatty acid esters with a carbon chain length of 16 or more is 2% or less, based on the total weight of all fatty acid esters in the mixture.

11. A fatty acid ester mixture of 2-ethylhexanol and fatty acids, comprising 2-ethylhexyl fatty acid esters having the following carbon chain distribution:
    (a) $C_{12}$: 60% or more, and
    (b) $C_{14}$: between 15% and 40%,
        both based on the total weight of all fatty acid esters in the mixture.

12. The fatty acid ester mixture according to claim 11, wherein $C_{12}$ 2-ethylhexyl fatty acid esters comprise 65% or more, and $C_{14}$ 2-ethylhexyl fatty acid esters comprise between 20% and 35%, of the mixture, both based on the total weight of all fatty acid esters in the mixture.

13. The fatty acid ester mixture according to claim 11, wherein $C_{12}$ 2-ethylhexyl fatty acid esters comprise 70% or more, and $C_{14}$ 2-ethylhexyl fatty acid esters comprise between 25% and 30%, of the mixture, both based on the total weight of all fatty acid esters in the mixture.

14. The fatty acid ester mixture according to claim 11, wherein the aggregate amount of 2-ethylhexyl fatty acid esters with a carbon chain length of 10 or less is 3% or less, based on the total weight of all fatty acid esters in the mixture.

15. The fatty acid ester mixture according to claim 11, wherein the aggregate amount of 2-ethylhexyl fatty acid esters with a carbon chain length of 10 or less is 2% or less, based on the total weight of all fatty acid esters in the mixture.

16. The fatty acid ester mixture according to claim 11, wherein the aggregate amount of 2-ethylhexyl fatty acid esters with a carbon chain length of 10 or less is 1% or less, based on the total weight of all fatty acid esters in the mixture.

17. The fatty acid ester mixture according to claim 11, wherein the aggregate amount of 2-ethylhexyl fatty acid esters with a carbon chain length of 16 or more is 8% or less, based on the total weight of all fatty acid esters in the mixture.

18. The fatty acid ester mixture according to claim 11, wherein the aggregate amount of 2-ethylhexyl fatty acid esters with a carbon chain length of 16 or more is 4% or less, based on the total weight of all fatty acid esters in the mixture.

19. The fatty acid ester mixture according to claim 11, wherein the aggregate amount of 2-ethylhexyl fatty acid esters with a carbon chain length of 16 or more is 3% or less, based on the total weight of all fatty acid esters in the mixture.

20. The fatty acid ester mixture according to claim 11, wherein the aggregate amount of 2-ethylhexyl fatty acid esters with a carbon chain length of 16 or more is 2% or less, based on the total weight of all fatty acid esters in the mixture.

21. An oil component for a cosmetic preparation comprising a fatty acid mixture according to claim 1.

22. An oil component for a pharmaceutical preparation comprising a fatty acid mixture according to claim 1.

* * * * *